United States Patent [19]

Watanabe et al.

[11] 4,255,421

[45] Mar. 10, 1981

[54] FORTIMICIN AMINOGLYCOSIDES, PROCESS FOR PRODUCTION THEREOF, AND USE THEREOF

[75] Inventors: Isamu Watanabe; Akio Iwasaki; Toshihito Mori, all of Higashimurayama, Japan

[73] Assignee: Kowa Company, Ltd., Nagoya, Japan

[21] Appl. No.: 85,058

[22] Filed: Oct. 12, 1979

[30] Foreign Application Priority Data

Oct. 18, 1978 [JP] Japan .................................. 53/127388
Jun. 20, 1979 [JP] Japan .................................. 54/76768

[51] Int. Cl.³ ...................... A61K 31/71; C07H 15/22
[52] U.S. Cl. ........................................ 424/180; 536/4; 536/17 R
[58] Field of Search ........................... 536/17 B, 17 R; 424/180

[56] References Cited

U.S. PATENT DOCUMENTS 4,124,756  11/1978  Martin et al. ....................... 536/17 R
4,169,942  10/1979  Mochida et al. .................... 536/17 R

*Primary Examiner*—Johnnie R. Brown
*Attorney, Agent, or Firm*—Wenderoth, Lind & Ponack

[57] ABSTRACT

Novel aminoglycosides of the following formula

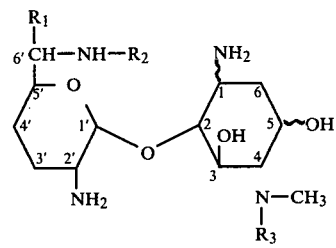

wherein $R_1$ and $R_2$ are identical or different and each represents a hydrogen atom or a methyl group, $R_3$ represents a hydrogen atom or an optionally substituted aminoacyl group having 2 to 4 carbon atoms in the acyl moiety, and when all of $R_1$, $R_2$ and $R_3$ are hydrogen atoms, the methylamino group at the 4-position is not oriented trans to the hydroxyl groups at the 3- and 5-positions; and acid addition salts thereof, which are useful as antibiotics; and process for producing compounds containing the same.

5 Claims, No Drawings

FORTIMICIN AMINOGLYCOSIDES, PROCESS FOR PRODUCTION THEREOF, AND USE THEREOF

This invention relates to novel aminoglycosides useful as antibiotics, a process for production thereof, and the use thereof.

More specifically, this invention relates to compounds of the following formula

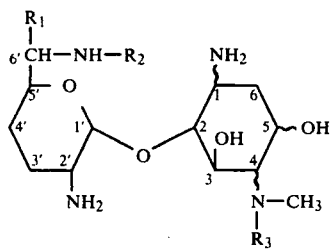
(I)-1 wherein $R_1$ and $R_2$ are identical or different and each represents a hydrogen atom or a methyl group, $R_3$ represents a hydrogen atom or an optionally substituted aminoacyl group having 2 to 4 carbon atoms in the acyl moiety, and when all of $R_1$, $R_2$ and $R_3$ are hydrogen atoms, the methylamino group at the 4-position is not oriented trans to the hydroxyl groups at the 3- and 5-positions; and acid addition salts thereof.

The invention also provides a process for producing compounds of the following formula

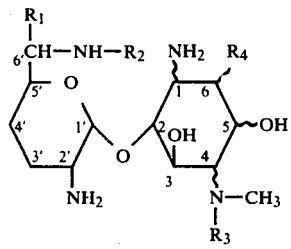
(I)

wherein $R_1$, $R_2$ and $R_3$ are as defined above, and $R_4$ represents a hydrogen atom or a hydroxyl group, which include known aminoglycosides of the following formula

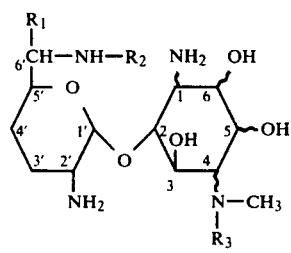
(I)-2 wherein $R_1$, $R_2$ and $R_3$ are as defined above, in addition to the novel aminoglycosides of formula (I)-1 in high yields by a decreased number of process steps with commercial advantage. The invention further relates to the use of the compounds of formula (I)-1 as antibiotics.

The present inventors have now found that the novel compounds of formula (I)-1 having a hydroxyl group at the 5-position exhibit higher antibiotic activity than compounds of formula (II)-1 which have $OCH_3$ at the 5-position, and that the compounds of formula (I)-1 can be advantageously produced in high yields by less process steps by treating the compounds of formula (II)-1 having a methoxy group at the 5-position with strong acids, optionally followed by acylation.

It has also been found that the amino glycosides of formula (I)-2, which are 5-de-o-methyl derivatives of an antibiotic known as fortimicin can be easily produced by less process steps in far higher yields than conventional methods by the same treatment with strong acids and optional acylation as mentioned above.

It is an object of this invention to provide novel compounds useful as antibiotics, a process for production thereof, and the use thereof.

Another object is to provide an improved process for producing the known amino glycosides of formula (I)-2.

The above and other objects and advantages of this invention will become more apparent from the following description.

The starting aminoglycoside used to produce the compound of formula (I) is expressed by the following formula

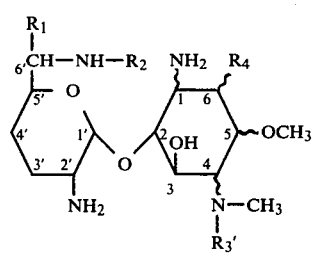
(II)

wherein $R_1$ and $R_2$ are identical or different, and each represents a hydrogen atom or a methyl group, $R_3'$ represents a moiety selected from the group consisting of a hydrogen atom, $-COCH_2NH_2$, $-COCH_2NH\text{-}CONH_2$ and $-COCH_2NHCHO$, and $R_4$ represents a hydrogen atom or a hydroxyl group.

Some compounds of the following formula

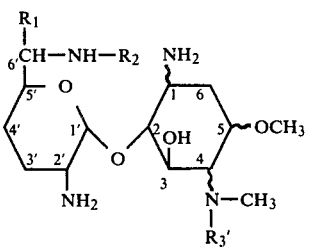
(II)-1 wherein all symbols are as defined in formula (II), which fall within the compounds of formula (II) are known. Specifically, among the starting compounds of formula (II)-1, those of the following formula

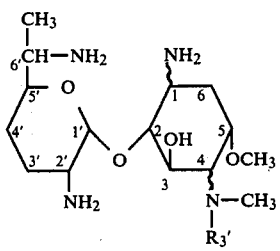

(A)

wherein R$_3'$ represents a moiety selected from the group consisting of hydrogen, —COCH$_2$NH$_2$, —COCH$_2$NHCONH$_2$ and —COCH$_2$NHCHO; and the acid addition salts thereof are known as antibiotic KA-6606 or sporaricin (for example, west German OLS No. 2813021 published on Oct. 5, 1978).

As described in detail in the German specification, the compounds of formula (A) can be produced by a process which comprises cultivating an antibiotic KA-6606-producing strain of the genus *Saccharopolyspora* and isolating the antibiotic KA-6606 from the culture broth. A typical strain is *Saccharopolyspora hirsuta* KC-6606 strain. This strain was deposited as FERM-P No. 3912 in Fermentation Research Institute, Agency of Industrial Science & Technology, Japan; as ATCC Number 20501 in American Type Culture Collection; and as DSM 1238 in German Collection of Microorganisms (Deutsche Sammulung von Microorganismen).

As disclosed in the German OLS No. 2813021, the known antibiotic KA-6606 can be further separated into four antibiotics KA-6606 I, KA-6606 II, KA-6606 III and KA-6606 IV, and the KA-6606 I, KA-6606 III and KA-6606 IV can be readily converted to KA-6606 II by treatment with alkalies or acids. Other antibiotics KA-6606 V and KA-6606 VI can be separated from antibiotic KA-6606. The molecular formulae and specific rotations of KA-6606 I to VI which belong to the starting compounds of formula (A) are given below.

| Antibiotics | Molecular formula | Specific rotation |
|---|---|---|
| KA-6606I | C$_{17}$H$_{35}$O$_5$N$_5$ | $[\alpha]_D^{27}$ + 104° (c1, H$_2$O) |
| KA-6606II | C$_{15}$H$_{32}$O$_4$N$_4$ | $[\alpha]_D^{27}$ + 139.5° (c1, H$_2$O) |
| KA-6606III | C$_{18}$H$_{36}$O$_6$N$_6$ | $[\alpha]_D^{27}$ + 103° (c1, H$_2$O) |
| KA-6606IV | C$_{18}$H$_{35}$O$_6$N$_5$ | $[\alpha]_D^{27}$ + 101° (c1, H$_2$O) |
| KA-6606V | C$_{15}$H$_{32}$O$_4$N$_4$ | $[\alpha]_D^{25}$ + 103° (c1, H$_2$O) |
| KA-6606VI | C$_{15}$H$_{32}$O$_4$N$_4$ | $[\alpha]_D^{25}$ + 54° (c1, H$_2$O) |

The groups R$_1$, R$_2$ and R$_3'$ of KA-6606 I to VI in formula (II)-1 are tabulated below.

| | R$_1$ | R$_2$ | R$_3'$ |
|---|---|---|---|
| KA-6606I | CH$_3$ | H | COCH$_2$NH$_2$ |
| KA-6606II | CH$_3$ | H | H |
| KA-6606III | CH$_3$ | H | COCH$_2$NHCONH$_2$ |
| KA-6606IV | CH$_3$ | H | COCH$_2$NHCHO |
| KA-6606V | CH$_3$ | H | H |
| KA-6606VI | CH$_3$ | H | H |

KA-6606II, V and VI differ in steric configurations at the 1- and 4-positions.

The specification of the German OLS 2813021 discloses in detail the separation of KA-6606 I and IV corresponding to formula (A). KA-6606 V and VI can be separated similarly during the separation of KA-6606 I to IV from crude KA-6606 obtained in the manner disclosed in the above German specification. For example, the crude KA-6606 is caused to be adsorbed to an adsorbent such as a weak acid-type cation exchange resin, CM-Sephadex or CM-cellulose, and eluted by a gradient method or a stepwise method using aqueous ammonia, an aqueous solution of ammonium carbonate, an aqueous solution of ammonium formate, etc. First, several trace components are eluted, and KA-6606 IV and then KA-6606 III are eluted as free bases. On further elution, KA-6606 I, VI and II substances are sequentially separated, and finally KA-6606 V is separated.

These components obtained can be purified by properly combining chromatography on cellulose, silica gel, etc. and chromatography on Sephadex series such as LH20. For example, they can be purified by chromatography with chloroform/methanol/17% ammonia solution (1:8:3) on a silica gel column.

The free bases obtained are then charged on a column of a strong base-type anion exchange resin such as Dowew 1X2 (a product of Dow Chemical Company) and eluted with water, for example. The active fractions were collected and lyophilized to obtain pure free bases. These free bases can be converted to the corresponding acid addition salts in a customary manner by adding inorganic acids such as hydrochloric acid, sulfuric acid, hydrobromic acid or carbonic acid, or organic acids such as acetic acid or oxalic acid.

Other compounds of formula (II)-1 used as a starting material in this invention are disclosed in the copending application of some of the present inventors, Ser. No. 056,313 filed on July 10, 1979.

These compounds are called antibiotics KA-7038 or sannamycin. The antibiotics KA-7038 can be produced by a process which comprises cultivating an antibiotic substance KA-7038-producing strain belonging to the genus Streptomyces, and isolating the antibiotic substance KA-7038 from the culture broth. A typical strain is Streptomyces sp. KC-7038. This strain KC-7038 was deposited as FERM-P No. 4388 in Fermentation Research Institute, Agency of Industrial Science & Technology, Japan; as ATCC number 31530 in American Type Culture Collection; and as DSM No. 1594 in German Collection of Microorganisms.

The substance KA-7038 can be further separated into seven antibiotics, KA-7038I, KA-7038II, KA-7038III, KA-7038IV, KA-7038V, KA-7038VI and KA-7038VII, and they can be readily converted to acid addition salts thereof by treatment with acids.

The formulae and physical and chemical properties of the starting KA-7038 I to VII are given below.

Substance KA-7038I:-

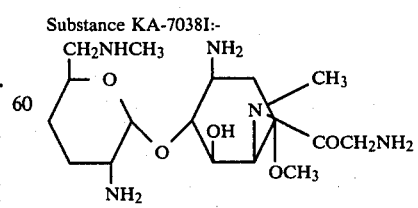

Molecular formula: C$_{17}$H$_{35}$O$_5$N$_5$
Specific rotation: $[\alpha]_D^{25}$ + 120.5°
(c 1, H$_2$O)
Melting point: 83°-90° C.
Substance KA-703°II:-

-continued

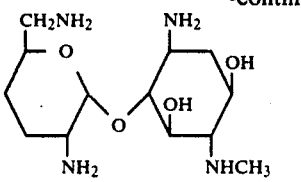

Molecular formula: $C_{13}H_{28}O_4N_4$
Specific rotation: $[\alpha]_D^{25} + 61°$ (c 1, $H_2O$)
Melting point: 85°–102° C.
Substance KA-7038III:-

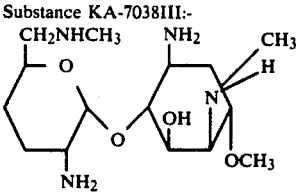

Molecular formula: $C_{15}H_{32}O_4N_4$
Specific rotation: $[\alpha]_D^{25} + 78°$ (c 0.5, $H_2O$)
Melting point: 74°–83° C.
Substance KA-7038IV:-

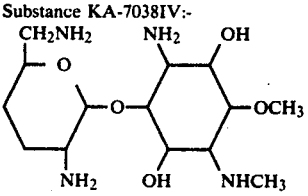

Molecular formula: $C_{14}H_{30}O_5N_4$
Specific rotation: $[\alpha]_D^{25} + 115°$ (c 0.1, $H_2O$)
Melting point: 78°–82° C.
Substance KA-7038V:-

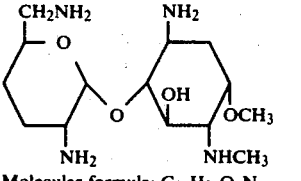

Molecular formula: $C_{14}H_{30}O_4N_4$
Specific rotation: $[\alpha]_D^{25} + 98°$ (c 0.5, $H_2O$)
Substance KA-7038VI:-

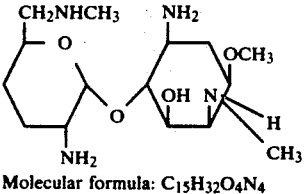

Molecular formula: $C_{15}H_{32}O_4N_4$
Specific rotation: $[\alpha]_D^{25} + 58°$ (c 1, $H_2O$)
Substance KA-7038VII:-

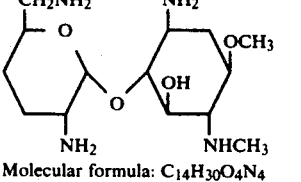

Molecular formula: $C_{14}H_{30}O_4N_4$
Specific rotation: $[\alpha]_D^{25} + 59°$ (c 1, $H_2O$)

In the present invention, the antibiotics KA-7038 can be obtained by cultivating a KA-7038-producing strain such as FERM-P No. 4388 strain or ATCC 31535 strain in a nutrient medium containing a carbon source, a nitrogen source and minerals, and separating KA-7038 from the culture broth.

Suitable culture media for use in fermenting the substance KA-7038-producing strain of the genus streptomyces comprise carbon and nitrogen sources and as optional ingredients, inorganic salts (minerals), very small amounts of heavy metals, etc.

Various carbon sources can be used, and examples of preferred carbon sources are glucose, starch, sucrose, fructose, dextrin, molasses and glycerol, which can be used either alone or as suitable mixtures. Hydrocarbons, alcohols, organic acids and vegetable oils can also be used if the strain used can utilize them as a carbon source.

Examples of nitrogen sources are soybean meal, yeast extract, dried yeast, peptone, meat extract, corn steep liquor, Casamino acid, Distiller's soluble, ammonium chloride, ammonium sulfate, ammonium nitrate, urea and sodium nitrate, which can be used either alone or as suitable mixtures. Examples of inorganic salts include sodium chloride, nitrates, calcium carbonate, potassium chloride, cobaltous chloride and ferrous sulfate.

Inorganic substances and organic substances (e.g., amino acids) which aid in the growth of the strain and promote the production of substance KA-7038 can also be added to the culture medium as required. When an aerating cultivation method is employed, an antifoamer such as fatty acid oils, silicone oils, cotton seed oil and paraffins can also be added to the culture medium.

Cultivation may be carried out in a solid medium. Preferably, however, as in the general process for producing antibiotics, a liquid cultivating method, especially a submerged cultivation method, is used. The cultivation is carried out under aerobic conditions, and the cultivation temperature is preferably about 20° to about 35° C., more preferably about 24° to about 27° C. Preferably, during the cultivation, the pH of the culture medium is maintained at about 4 to about 10. The cultivation period is generally about 2 days to about 10 days.

As a result of the cultivation, the substance KA-7038 is produced and accumulated in the culture broth. When the amount of the substance KA-7038 produced in the culture broth reaches a maximum, the cultivation is stopped. The substance KA-7038 can be collected from the culture broth.

Since the substance KA-7038 is a water-soluble basic substance but difficultly soluble in common organic solvents, it can be separated from the culture broth by utilizing the procedures which are customarily used in isolating and purifying watersoluble basic antibiotics. For example, there can be used an adsorption desorption method using and ion exchange resin, active carbon etc.; column chromatographic method using cellulose, silica gel, alumina, etc.; and a method for extracting with butanol, amyl alcohol, etc. using a higher fatty acid as an adjuvant.

For example, if the culture broth filtrate is charged on a column of a weak acidic cation exchange resin, the substance KA-7038 is adsorbed to it. The substance KA-7038 is then isolated by elution with a 0.1–3.0 N alkali or acid. The resulting active eluate may be lyophilized to afford a crude powder of substance KA-7038.

Examples of the weak acidic cation exchange resin used to recover the substance KA-7038 are Amberlite IRC-50, IRC-84 and CG-50 (Rohm & Haas Co.); and Diaion WK-10 and WK-20 (Mitsubishi Chemical Co., Ltd.). Examples of alkalies that can be used for the elution are ammonium hydroxide solution, and an aqueous solution of sodium hydroxide. Examples of the acids are formic acid, hydrochloric acid and sulfuric acid. Another example of the recovering method comprises adjusting the pH of the culture broth filtrate to 7 to 9, contacting the filtrate with active carbon to cause the substance KA-7038 to adsorb the active carbon, and eluting the substance with acidic water.

The substance KA-7038 that can be isolated by the methods described above can be separated into KA-7038 I, II, III, IV, V, VI and VII by dissolving it in water charging it on a column of an adsorbent such as a weak acidic ion exchange resin of the type described above or a weak acidic ion exchange such as CM-sephadex or CM-cellulose to cause the substance to be adsorbed to the adsorbent, and then eluting it with an alkaline aqueous solution such as dilute ammonium hydroxide, or an aqueous solution of ammonium carbonate or ammonium formate by a gradient method or a stepwise method. According to this separating procedure, substance KA-7038 IV, substance KA-7038 VII, substance KA-7038 I, substance KA-7038 II, substance KA-7038 VI, substance KA-7038 III and substance KA-7038 V as free bases are separated successively.

The resulting substances KA-7038 I, II, III, IV, V, VI and VII separated can be in powder form by concentrating the eluate and lyophilizing the condensate. They can be purified by column chromatography on, for example, cellulose, strong basic anion exchange resin. For example, dissolving the powder in water, causing them to be adsorbed to a column of a strong basic anion exchange resin such as Dowex 1x2 (Dow Chemical), eluting them with deionized water, collecting active fractions, and lyophilizing the collected fractions. These substances obtained from KA-7038 as free base can be converted to their acid addition salts by treatment with pharmaceutically acceptable inorganic or organic acids. Examples of such acids are inorganic acids such as sulfuric acid, hydrochloric acid, hydriodic acid, phosphoric acid, carbonic acid, nitric acid etc., and organic acids such as acetic acid, fumaric acid, maleic acid, citric acid, mandelic acid and succinic acid.

The substance KA-7038 III has the structural formula of the substance KA-7038 I in which the glycyl group -COCH$_2$NH$_2$ is split off. Therefore, the substance KA-7038 III can also be obtained by treating the substance KA-7038 I with alkalies or acids to decompose the substance KA-7038 I and convert it to substance KA-7038 III. This conversion can be effected by treating the substance KA-7038 I with a 0.1-4 N aqueous solution of an alkaline reagent such as sodium hydroxide or barium hydroxide or with a 0.1-1 N aqueous solution of an acidic reagent such as hydrochloric acid or sulfuric acid.

In the case of using the alkaline reagent, a strong basic anion exchange resin [e.g., Amberlite IRA 400 (OH$^-$ form) or Dowex 1x2 (OH$^-$ form)]may be added, and the reaction can be performed in the suspended state. Likewise, when the acidic reagent is used, a strong acidic cation exchange resin such as Amberlite IR 120 (H$^+$ form) or Dowex 50x8 (H$^+$ form) may be added, and the reaction can be performed in the suspended state. The reaction can be performed usually at about 30° to 100° C. for about 0.5 to 3 hours.

According to this invention, there is provided a novel commercially advantageous process for producing known antibiotics de-O-methyl-fortimicins (U.S. Pat. No. 4,124,756) of the following formula

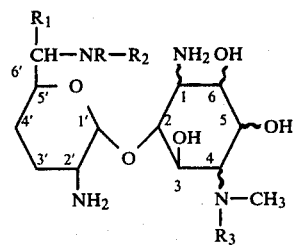

wherein R$_1$, R$_2$ and R$_3'$ are as defined hereinabove, from known antibiotics fortimicins (disclosed, for example, in U.S. Pat. Nos. 3931400, 3976768 and 4048015, West German OLS Nos. 2418349 and 2748530, and Japanese Laid-Open Patent Publication No. 95548/79) of the following formula

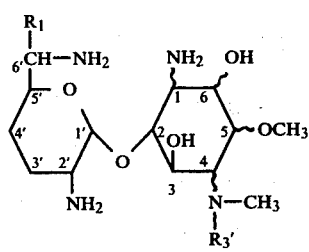

wherein R$_1$ and R$_3'$ are as defined hereinabove.

According to the method disclosed in U.S. Pat. No. 4,124,756 for producing the 5-de-o-methyl derivatives [formula (I)-2] of the fortimicins of formula (II)-2, fortimicin B (corresponding to formula (II)-2 in which R$_1$ is methyl and R$_3'$ is hydrogen), for example, is reacted with an excess amount of metallic lithium in a solvent such as ethylamine or ethylenediamine to form de-O-methyl-fortimicin B (corresponding to formula (I)-2 in which R$_1$ is methyl and R$_3'$ is hydrogen). When the primary amino group of the de-O-methyl-fortimicin B is protected and the methylamino group at the 4-position is acylated, followed by splitting off the protective group for the amino group, a compound corresponding to formula (I)-2 in which R$_3'$ is, for example, a glycyl group —COCH$_2$NH$_2$ which is de-O-methyl fortimicin A is obtained. Reduction of this compound yields de-O-methyl-4-N-($\beta$-aminoethyl)fortimicin B which corresponds to formula (I)-2 in which R$_3'$ is a $\beta$-aminoethyl group.

However, this method is commercially disadvantageous because the yield in the first step of cleaving the methyl ether is only about 1.3%. According to this invention, de-O-methyl products can be obtained in commercially feasible yields from fortimicins and KA-6606 and KA-7038 substances having a structure similar thereto. Specifically, the compounds of formula (II)-2 can be obtained in a yield as high as or more than 10 times that obtained in the aforesaid known method by treating the compound of formula (II) with strong acids.

The present invention also provides a process for preparing a compound of the following formula

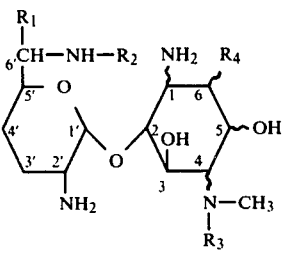

(I)

wherein $R_1$ and $R_2$ are identical or different, and each represents a hydrogen atom or a methyl group, $R_3$ represents a hydrogen atom, or an aminoacyl group having 2 to 4 carbon atoms in the acyl moiety, said aminoacyl group being optionally substituted, and $R_4$ represents a hydrogen atom or a hydroxyl group, or an acid addition salt thereof, which comprises treating a compound of the followin formula

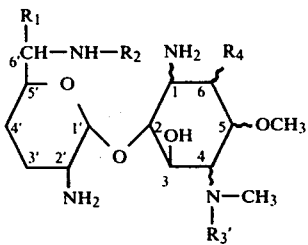

(II)

wherein $R_1$, $R_2$ and $R_4$ are as defined above, and $R_3'$ represents a moiety selected from the group consisting of a hydrogen atom, $-COCH_2NH_2$, $-COCH_2NH-CONH_2$ and $-COCH_2NHCHO$, with a strong acid, and when a compound of formula (I) wherein $R_3$ is a hydrogen atom is obtained, protecting the amino or methylamino groups at the 1-, 2'- and 6'-positions of the resulting compound, then acylating it with an optionally substituted amino acid having 2 to 4 carbon atoms in the acyl moiety and a protected amino group or a reactive derivative thereof, and then splitting off the protective group, and if desired, converting the product to an acid addition salt.

Of the compounds of formula (I), those of formula (I)-1 given hereinabove or the acid addition salts thereof are novel antibiotics.

In the practice of the process of this invention, the compound of formula (II) or its protected product at the amino or the methylamino groups at the 1-, 2'- and 6'-positions is reacted with a strong acid in the presence or absence of a solvent. This reaction induces the cleavage of the methyl ether at the 5-position and the splitting off of $R_3'$ bonded to the methylamino group at the 4-position when it is an acyl group. Thus, a compound of formula (I) in which a hydroxyl group is present at the 5-position and $R_3$ is a hydrogen atom can be obtained.

Examples of the strong acid are strong mineral acids such as hydrobromic acid, hydrochloric acid, hydriodic acid, hydrofluoric acid, sulfuric acid and phosphoric acid; strongly acidic organic acids such as p-toluenesulfonic acid and trifluoromethanesulfonic acid; and Lewis acids such as boron trichloride and boron trifluoride. When a Lewis acid is used, the reaction is preferably carried out in an ahydrous condition. In other cases, the reaction is preferably carried out in aqueous solution.

For example, dichloromethane can be used as an anhydrous solvent.

The reaction can be carried out, for example, at room temperature to about 200° C. Usually, the reaction ends in about 1 hour to about 30 days. The product can be separated and purified by an ordinary column chromatographic method, for example by using a cation exchange resin. Acylation of the methylamino group at the 4-position of the resulting compound of formula (I) in which $R_3$ is a hydrogen atom affords a compound of formula (I) in which $R_3$ is an acyl group. A preferred acyl group represented by $R_3$ is an aminoacyl group which may have a substituent and in which the acyl moiety has 2 to 4 carbon atoms. Examples of the substituent are lower alkyl groups, a formyl group ($-CHO$), and a carbamoyl group ($-CONH_2$).

In performing the acylation, the amino or methylamino groups at the 1-, 2'- and 6'-positions of the compound of formula (I) in which $R_3$ is a hydrogen atom and $-OH$ is present at the 5-position are protected, and then an optionally substituted amino acid (preferably protected) or its reactive derivative for forming the desirable acyl group is caused to act on the protected compound to acylate the methylamino group at the 4-position. Subsequent deprotection can afford the compound of formula (I) as a free base. If desired, the product is treated with an acid to convert it to an acid addition product.

Protective groups for an amino or methylamino group may be those used ordinarily in peptide synthesis. For example, when an active ester such as a substituted phenyl ester (e.g., monobenzyl carbonate), N-oxysuccinimide ester or N-oxyphthalimide ester is used, only the amino or methylamino groups at the 1-, 2'- and 6'-positions are protected by a benzyloxycarbonyl group. The presence of a metal compound such as nickel acetate, cobaltous acetate and copper acetate during the protecting reaction is preferred. Substituted benzyloxycarbonyl groups and tertiary butoxy carbonyl group may also be used as protective groups. When the methylamino group at the 4-position is simultaneously protected, it can be liberated by reacting the product with an alkali to form a cyclic carbamate with the hydroxyl group adjacent to the methylamino group at the 4-position, and then hydrolyzing it.

The aforesaid introduction of a protective group into the amino or methylamino groups can be effected, for example, by causing the active ester to act on the compound of formula (I) wherein $R_3$ is hydrogen at a temperature of about 0° to about 100° C. preferably in the presence of a metal compound, the amount of the active ester being about 3 to about 10 moles per mole of the compound of formula (I). The reaction can be terminated usually in about 0.5 to about 20 hours.

According to the method of this invention, an acyl group is introduced, if desired, into the methylamino group at the 4-position of the compound of formula (I) in which $R_3$ is hydrogen and the amino or methylamino groups at the 1-, 2'- and 6'-positions are protected. The acylation can be performed by using a conventional peptide synthesizing technique. Acylation is carried out using an amino-protected amino acid or another substituted carboxylic acid or a reactive derivative thereof. Examples of the reactive derivative are acid halides, active esters such as a phenyl ester, cyanomethyl ester, N-oxysuccinimide ester or N-oxyphthalimide ester, acid azides, acid anhydrides, mixed acid anhydrides, and other compounds which are used in the synthesis of peptides. Protective groups for the amino group of the amino acid may be the same as those exemplified hereinabove for the amino or methylamino groups of the compound of formula (I) in which $R_3$ is hydrogen. Preferably, quite the same protective groups should be used.

The acylation reaction can be performed, for example, at a temperature of about 0° to about 100° C. in a solvent such as methanol, dioxane, acetonitrile and dichloromethane by using about 1 to about 10 moles of an acylating agent per mole of the compound to be acylated. Usually, the reaction can be terminated in about 0.5 to about 20 hours.

Preferably, the protective groups for the amino groups are split off from the protected compound of formula (I) preferably by a catalytic reducing method. Suitable catalysts for this purpose include palladium, platinum, Raney nickel, rhodium, ruthenium, and nickel.

Splitting off of the protective groups by catalytic reduction can be performed, for example, by reacting the protected compound in a solvent such as acetic acid in the presence of a catalyst at a temperature of about 0° to about 80° C. for about 1 to about 50 hours. The hydrogen pressure at this time may be normal or atmospheric pressure or an elevated pressure.

If further required, the acyl group of the acylated product may be reduced to produce a compound in which $R_3$ is a substituted alkyl group. Preferably, the reducing reaction is carried out before the protecting groups for the amino groups are split off. Reducing methods using reducing agents such as lithium aluminum hydride, sodium borohydride and diborane can be utilized.

In the present invention, the compound of formula (I) that can be obtained from the compound of formula (II) in the above manner can be isolated and purified in a customary manner. Column chromatography is preferred. Preferred adsorbents for this purpose are cation exchange resins such as CM-Sephadex, Amberlite IRC-50, Amberlite IRC-84, Amberlite CG-50, and carboxymethyl cellulose. Development can be performed by a gradient method or a stepwise method using an alkaline aqueous solution such as an aqueous solution of ammonia or an aqueous solution of ammonium formate as a developing solvent. The active fractions are collected from the eluates, and lyophilized to obtain the compound of formula (I) in pure form.

Depending upon the purifying operation, the desired product (I) may also be obtained in the form of an acid addition salt. The compound (I) as a free base can be converted to an acid addition salt thereof, preferably a pharmaceutically acceptable acid addition salt thereof, in a customary manner. Acids for this purpose include, for example, inorganic acids such as sulfuric acid, hydrochloric acid, hydrobromic acid, hydroidic acid, phosphoric acid, carbonic acid and nitric acid, and organic acids such as acetic acid, fumaric acid, malic acid, citric acid, mandelic acid and succinic acid.

According to the process of this invention, the desired compounds of formula (I) having antibacterial activity can be obtained easily and in good yields from fortimicins or KA-6606 and KA-7038 substances having a structure similar to the fortimicins.

The compounds of formula (I)-1 are compounds not described heretofore in the literature. The compounds of formula (I) including the compounds of formula (I)-1 exhibit superior antibiotic activity, and are useful in the field of medicines for man and animals, and also as intermediates for the synthesis of derivatives.

Thus, the present invention can provide an antibiotic composition comprising the novel compound of formula (I)-1.

Specifically, according to this invention, there is provided an antibiotic composition composed of (i) an antibiotically effective amount of a compound having the following formula

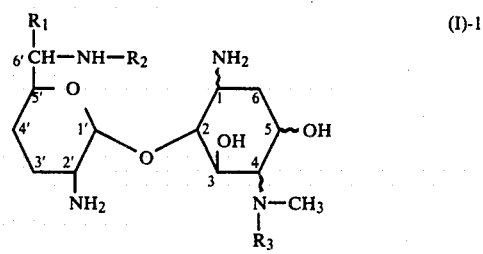

wherein $R_1$ and $R_2$ are identical or different, and each represents a hydrogen atom or a methyl group, and $R_3$ represents a hydrogen atom or an optionally substituted aminoacyl group having 2 to 4 carbon atoms in the acyl moiety, and when all of $R_1$, $R_2$ and $R_3$ are hydrogen atoms, the methylamino group at the 4-position is not oriented trans to the hydroxyl groups at the 3- and 5-positions, or a pharmaceutically acceptable acid addition salt thereof, and (ii) a pharmaceutically acceptable diluent or carrier.

The amount of the compound (I)-1 is, for example, about 0.01 to about 99.5% by weight, based on the weight of the composition.

The antibiotic composition of this invention may be in any of the dosage forms usually employed, but injecting preparations and capsules are especially preferred.

Preferably, like known water-soluble basic antibiotics, an injectable is prepared by filling a lyophilized powder of the antibiotic into a vial, preferably together with a stabilizer, and in use, the contents of the vial are dissolved in a dissolving liquid for administration.

The diluent or carrier includes, for example, liquid diluents such as distilled water for injection and physiological isotonic solution, and solid carriers such as lactose, starch, white sugar, glucose, crystalline cellulose, calcium carbonate, kaolin, D-mannitol, magnesium metasilicate aluminate, calcium sulfate, calcium phosphate and bentonite. Addition of stabilizers such as acidic sodium bisulfite is also preferred.

The dosage of the antibiotic substance of this invention can be suitably selected, and is, for example, about 0.01 to about 100 mg/kg/day.

Thus, according to this invention, there can be provided antibiotic compositions for animals other than human, such as poultry, domesticated animals and cultivated fish, and antibiotic compositions for human. These compositions are useful as antibacterial agents having a broad antibacterial spectrum.

Table 1 below summarizes the antibacterial spectra of several examples of the compound of formula (I)-1 and starting materials therefor.

TABLE 1

| | KA-6606I | De-O-methyl KA-6606I | 4-N-glycyl KA-6606VI | De-O-methyl-4-N-glycyl KA-6606VI | KA-7038I | De-O-methyl KA-7038I |
|---|---|---|---|---|---|---|
| *Staphylococcus aureus* 209P | 0.2 | 0.2 | 0.39 | 0.39 | 0.39 | 0.39 |
| *Bacillus subtilis* ATCC 6633 | 0.2 | <0.1 | 0.20 | 0.20 | 0.20 | <0.1 |
| *Bacillus cereus* | 1.56 | 0.78 | 0.78 | 0.78 | 1.56 | 0.39 |
| *Bacillus anthracis* | 0.2 | <0.1 | 0.20 | 0.20 | 0.20 | <0.1 |
| *Streptococcus faecalis* | 25 | 25 | 25 | 25 | 50 | 100 |
| *Escherichia coli* NIHJ | 1.56 | 1.56 | 1.56 | 1.56 | 3.13 | 3.13 |
| *Escherichia coli* ML1410 | 1.56 | 1.56 | 3.13 | 3.13 | 1.56 | 1.56 |
| *Escherichia coli* ML1410R-81 (resistant to kanamycin, streptomycin and lividomycin) | 3.13 | 1.56 | 6.25 | 3.13 | 6.25 | 3.13 |
| *Escherichia coli* ML1410R-82 (resistant to kanamycin, streptomycin and butirosin) | 3.13 | 3.13 | 6.25 | 6.25 | 12.5 | 6.25 |
| *Escherichia coli* ML1410R-101 (resistant to gentamicin, tobramycin and kanamycin) | 1.56 | 1.56 | 3.13 | 3.13 | 6.25 | 3.13 |
| *Proteus vulgaris* OX-19 | 0.78 | 0.78 | 1.56 | 1.56 | 3.13 | 3.13 |
| *Klebsiella pneumoniae* PCI 602 | 0.78 | 0.78 | 0.78 | 0.78 | 1.56 | 0.78 |
| *Pseudomonas aeruginosa* Shibata | 3.13 | 0.78 | 6.25 | 1.56 | 6.25 | 1.56 |
| *Pseudomonas aeruginosa* A3 | 3.13 | 0.78 | 6.25 | 3.13 | 12.5 | 3.13 |
| *Pseudomonas aeruginosa* No. 12 | 0.39 | 0.39 | 0.78 | 0.78 | 1.56 | 0.78 |
| *Pseudomonas aeruginosa* TI-13 | 3.13 | 0.78 | 3.13 | 3.13 | 6.25 | 1.56 |
| *Pseudomonas aeruginosa* K-11 (resistant to kanamycin) | 6.25 | 1.56 | 6.25 | 6.25 | 12.5 | 3.13 |
| *Pseudomonas aeruginosa* No. 157 | 6.25 | 1.56 | 3.13 | 1.56 | 6.25 | 1.56 |
| *Pseudomonas aeruginosa* No. 315 (resistant to gentamicin tobramycin and amikacin) | 6.25 | 3.13 | 12.5 | 6.25 | 25 | 6.25 |
| *Proteus inconstans* | 1.56 | 1.56 | 1.56 | 1.56 | 6.25 | 6.25 |
| *Serratia marcescens* | 3.13 | 1.56 | 0.78 | 1.56 | 1.56 | 0.78 |

The following examples show the production of the compounds of this invention and the production of known de-O-methyl-fortimicin by the process of this invention.

EXAMPLE 1

De-O-methyl-KA-6606 II

KA-6606 II as a free base (1.1 g) was dissolved in 100 ml of 48% hydrobromic acid, and the solution was heated in a sealed tube at 90° C. for 4 hours. The reaction mixture was concentrated to dryness under reduced pressure. The residue was dissolved in water, and neutralized with conc. aqueous ammonia. The solution was charged on a column packed with 400 ml of CM-Sephadex C-25 (NH$_4$+ form), and eluted with aqueous ammonia of a concentration varying gradually from 0.05 N to 0.5 N. Fractions containing de-O-methyl-KA-6606 II were collected, and treated in a customary manner to afford 620 mg of de-O-methyl-KA-6606 II as a colorless compound having the following formula.

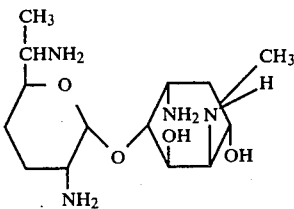

Specific rotation: $[\alpha]_D^{25} +140°$ (c2, H$_2$O).

NMR: δ D$_2$O ppm: 1.53 (3H, d, J=6.3 Hz, C-CH$_3$); 2.88 (3H, s, N-CH$_3$); 5.46 (1H, d, J=3.4 Hz, anomeric H).

Elemental analysis: for C$_{14}$H$_{30}$N$_4$O$_4$.H$_2$O Calculated (%): C 49.98; H 9.59; N 16.65. Found (%): C 49.69; H 9.73; N 16.48.

EXAMPLE 2

(A)

Tetrakis-N-benzyloxycarbonyl-de-O-methyl-KA-6606 I

De-O-methyl-KA-6606 II as a free base (60 mg) was dissolved in 5 ml of methanol, and at −10° C., 75 mg of N-benzyloxycarbonyloxy succinimide was added. The mixture was stirred. At the end of 1 hour, and 2 hours respectively, 30 mg and 20 mg of the aforesaid active ester were added. The mixture was further stirred at the same temperature for 2 hours. The reaction mixture was concentrated under reduced pressure. The residue was dissolved in 10 ml of chloroform, washed with water, and dried, followed by distilling off the solvent.

The residue was dissolved in 3.5 ml of dioxane, and 0.2 ml of triethylamine and 100 mg of N-hydroxysuccinimidyl-N-benzyloxycarbonylglycine were added. The mixture was heated at 60° C. overnight. The reaction mixture was concentrated to dryness. The residue was dissolved in 10 ml of chloroform, washed with water and dried, followed by distilling off the solvent. The residue was chromatographed on a silica gel column using chloroform-methanol (50:1) as an eluent, and finished in a customary manner to afford 62 mg of tetrakis-N-benzyloxycarbonyl-de-O-methyl-KA-6606 I as a colorless solid.

Specific rotation: $[\alpha]_D^{25} +37°$ (c2, H$_2$O).

NMR: δ CDCl$_3$, ppm: 1.01 (3H, d, J=6.5 Hz, C-CH$_3$); 2.91 (3H, s, N-CH$_3$).

IR: $\nu_{max}^{CHCl_3}$ cm$^{-1}$ 1640 (amide I).

Elemental analysis: for C$_{48}$H$_{57}$N$_5$O$_{13}$ Calculated (%): C 63.22; H 6.30; N 7.68. Found (%): C 63.28; H 6.35; N 7.55.

(b) De-O-methyl-KA-6606 I

The tetrakis-N-benzyloxycarbonyl-de-O-methyl-KA-6606 I (60 mg) obtained in (a) above was dissolved in 1.2 ml of acetic acid, and hydrogenolyzed in the presence of 30 mg of palladium black at room temperature and atmospheric pressure. The catalyst was removed by filtration, and the filtrate was diluted with 100 ml of water and neutralized in conc. aqueous ammonia. The solution was charged on a column packed with 10 ml of CM-Sephadex C-25 (NH$_4$+ form), and eluted by a gradient method using aqueous ammonia of a concentration varying gradually from 0.05 N to 0.5 N. Fractions containing the desired compound were collected, and lyophilized to afford 21 mg of de-O-methyl-KA-6606 I as a colorless solid having a melting point of 172° to 175° C. (decomp.) and the following formula.

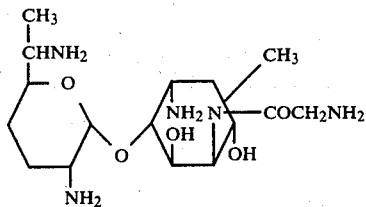

Elemental analysis: for C$_{16}$H$_{33}$N$_5$O$_5$.H$_2$CO$_3$.H$_2$O. Calculated (%): C 44.83; H 8.19; N 15.38. Found (%): C 44.47; H 8.38; N 15.05.

The hydrochloride of this product obtained by a conventional method has the following properties.

Specific rotation: $[\alpha]_D^{25} +110°$ (c2, H$_2$O)

NMR: δ D$_2$O ppm: 1.83 (3H, d, J=6.6 Hz, C-CH$_3$); 3.63 (3H, s, N-CH$_3$); 6.03 (1H, d, J=3.6 Hz, anomeric H).

EXAMPLE 3

De-O-methyl-fortimicin B

Fortimicin B as a free base (100 mg) was dissolved in 5 ml of 52% hydriodic acid, and reacted in a sealed tube at 37° C. for 10 days. After the reaction, the hydriodic acid was distilled off. The residue was diluted with water, and neutralized with aqueous ammonia. The solution was charged on a column of CM-Sephadex C-25 NH$_4$+ form), and eluted by a concentration gradient method using aqueous ammonia of a concentration varying gradually from 0.05 N to 0.5 N. Fractions containing the desired product were collected, and concentrated to dryness to afford 16 mg of de-O-methyl fortimicin B as a free base having the following formula.

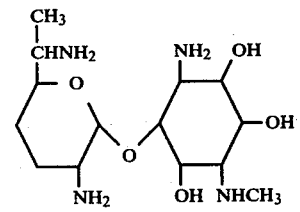

Specific rotation: $[\alpha]_D^{23} +43°$ (c1, H$_2$O).

NMR: δ D$_2$O ppm: 1.50 (3H, d, J=6.5 Hz, CH-CH$_3$); 2.83 (3H, s, N-CH$_3$); 5.54 (1H, d, J=3.5 Hz, anomeric H).

EXAMPLE 4

De-O-methyl-fortimicin A

The same procedure as in Example 2, (a) was repeated except that 30 mg of de-O-methyl fortimicin B as a free base was used. There was obtained 34 mg of tetrakis-N-benzyloxycarbonyl-de-O-methyl fortimicin A as a colorless solid.

The product was dissolved in 1.0 ml of acetic acid, and hydrogenolyzed and purified in the same way as in Example 2, (b) to afford 10 mg of de-O-methyl fortimicin A as a colorless solid having the following formula:

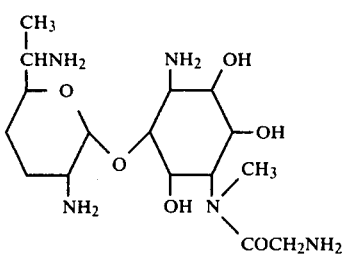

Elemental analysis: for $C_{16}H_{33}N_5O_6 \cdot H_2O$. Calculated (%): C 46.93; H 8.62; N 17.10. Found (%): C 46.66; H 8.47; N 16.81.

The hydrochloride produced from the free base in a customary manner had the following properties.

Specific rotation: $[\alpha]_D^{23} + 82°$ (c1, $H_2O$).

NMR: δ $D_2O$ ppm: 1.80 (3H, d, J=6.5 Hz, C-C$\underline{H}_3$); 3.60 (3H, s, N-C$\underline{H}_3$); 5.78 (1H, d, J=3.5 Hz, anomeric $\underline{H}$).

EXAMPLE 5

De-O-methyl-KA-6606 II

KA-6606 II as a free base (100 mg) was suspended in 5 ml of dichloromethane, and 5 g of boron trichloride was added at −80° C. The mixture was allowed to stand at the same temperature for 1 hour. Then, at room temperature, it was allowed to stand overnight. The reacreaction mixture was concentrated to dryness, and methanol was added to the residue. The mixture was again concentrated to dryness. This operation was repeated three times.

The resulting residue was dissolved in 10 ml of water, and the solution was charged on a column packed with 40 ml of CM-Sephadex C-25 ($NH_4^+$ form), and eluted by a concentration gradient method using aqueous ammonia of a concentration gradually varying from 0.05 N to 0.5 N. Fractions containing de-O-methyl-KA-6606 II were collected, and finished in a customary manner to obtain 15 mg of a colorless substance. The properties of this product were identical with those of the de-O-methyl-KA-6606 II obtained in Example 1.

EXAMPLE 6

De-O-methyl-KA-6606 VI

KA-6606 VI as a free base (350 mg) was dissolved in 3.5 ml of 56% hydriodic acid, and heated at 60° C. in a sealed tube for 4 hours. The reaction mixture was concentrated to dryness under reduced pressure. The residue was dissolved in water, and neutralized with conc. aqueous ammonia. The solution was charged on a column packed with 30 ml of CM-Sephadex C-25 ($NH_4^+$ form), and eluted with aqueous ammonia of a concentration varying gradually from 0.25 N to 0.35 N. Fractions containing the desired product were collected, and concentrated to dryness to obtain 265 mg of de-O-methyl-KA-6606 VI having the following formula.

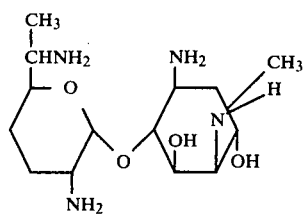

Elemental analysis: for $C_{14}H_{30}N_4O_4 \cdot H_2O$. Calculated (%): C 49.98; H 9.59; N 16.65. Found (%): C 49.65; H 9.44; N 16.61.

Specific rotation: $[\alpha]_D^{23} + 87°$ (c1, $H_2O$).

NMR: δ $D_2O$ ppm: 1.54 (3H, d, J=6.5 Hz, C-C$\underline{H}_3$); 2.85 (3H, s, N-C$\underline{H}_3$); 5.56 (1H, d, J=3.3 Hz, anomeric $\underline{H}$).

EXAMPLE 7

(a)

1,2',6'-tris-N-benzyloxycarbonyl-4-N-benzyloxycarbonylglycyl-de-O-methyl-KA-6606 VI De-O-methyl-KA-6606 VI (163 mg) was dissolved in 5 ml of methanol, and 273 mg of nickel acetate was added. The mixture was stirred at room temperature for 30 minutes, and then 454 mg of N-benzyloxycarbonyloxysuccinimide was added. The mixture was stirred at the same temperature for 2 hours. Conc. aqueous ammonia (2.5 ml) was added to the reaction mixture, and the mixture was stirred for 2 hours. The reaction mixture was concentrated under reduced pressure, and the residue was dissolved in 20 ml of chloroform and 3 N aqueous ammonia. The solution was shaken. The chloroform layer was separated, washed twice with 3 N aqueous ammonia and twice with water, and dried, followed by distilling off the solvent.

The residue was dissolved in 9 ml of dioxane, and 330 mg of 2,4-dinitrophenyl ester of N-benzyloxycarbonylglycine and 0.3 ml of triethylamine were added, and the mixture was heated at 60° C. for 1 hour. To the reaction mixture was added 1 ml of conc. aqueous ammonia, and the mixture was allowed to stand for 1 hour. The solvent was then distilled off. The residue was dissolved in 20 ml of chloroform, and washed three times with 0.5 N aqueous sodium hydroxide solution and twice with water, and dried, followed by distilling off the solvent. The residue was chromatographed on a silica gel column using chloroform/methanol (50:1) as an eluent. Fractions containing the desired product were collected, and concentrated to afford 288 mg of 1,2',6'-tris-N-benzyloxycarbonyl-4-N-benzyloxycarbonylglycycl-de-O-methyl-KA-6606 VI as a colorless solid.

Elemental analysis: for $C_{48}H_{57}N_5O_{13}$: Calculated (%): C 63.22; H 6.30; N 7.68. Found (%): C 63.43; H 6.21; N 7.44.

Specific rotation: $[\alpha]_D^{23} + 32°$ (c 1, $CHCl_3$).

NMR: δ $CDCl_3$ ppm: 2.92 (3H, s, N-C$\underline{H}_3$); 1.21 (3H, d, J=6 Hz, CH-C$\underline{H}_3$).

(b) De-O-methyl-4-N-glycyl-KA-6606 VI

The 1,2',6'-tris-N-benzyloxycarbonyl-4-N-benzyloxycarbonylglycyl-de-O-methyl-KA-6606 VI (288 mg) obtained in (a) above was dissolved in 4 ml of acetic acid, and 50 mg of palladium black was added. The above compound was then catalytically reduced at room temperature. The reaction mixture was filtered.

The filtrate was diluted with 400 ml of water, and neutralized with aqueous ammonia. The solution was charged on a column of CM-Sephadex C-25 (NH$_4^+$ form), and eluted by a concentration gradient method using aqueous ammonia of a concentration gradually varying from 0.05 N to 0.35 N. Fractions containing the desired product were collected, and lyophilized to afford 105 mg of de-O-methyl-4-N-glycyl-KA-6606 VI as a colorless solid having the following formula.

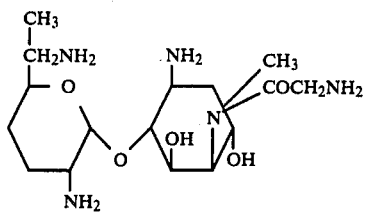

Elemental analysis: for C$_{16}$H$_{33}$N$_5$O$_5$.H$_2$O Calculated (%): C 48.84; H 8.97; N 17.80. Found (%): C 48.55; H 8.83; N 17.48.

Specific rotation: $[\alpha]_D^{23} +115°$ (C 1, H$_2$O).

NMR: δ D$_2$O ppm: 1.52 (3H, d, J=6.5 Hz, C-C$\underline{H}_3$); 3.62 (3H, s, N-C$\underline{H}_3$); 5.40 (1H, d, J=3 Hz, anomeric $\underline{H}$).

EXAMPLE 8

De-O-methyl-KA-6606 VI

KA-6606 VI (100 mg) was dissolved in 5 ml of 48% hydrobromic acid, and the solution was allowed to stand at 37° C. for 10 days. The reaction mixture was concentrated to dryness at below 37° C. The residue was dissolved in 50 ml of water, and neutralized with aqueous ammonia. The solution was charged on a column of CM- Sephadex C-25 (NH$_4^+$ form), and eluted by a concentration gradient method using aqueous ammonia of a concentration varying gradually from 0.05 N to 0.5 N to afford 19 mg of de-O-methyl-KA-6606 VI. The properties of the product were identical with those of the de-O-methyl-KA-6606 VI obtained in Example 6.

EXAMPLE 9

1,2',6'-tris-N-benzyloxycarbonyl-4-N-benzyloxycarbonylglycyl-de-O-methyl-KA-6606 VI De-O-methyl-KA-6606 VI (19 mg) was dissolved in 0.8 ml of methanol, and 90 mg of benzyl p-nitrophenyl carbonate was added. The mixture was stirred overnight at room temperature. To the reaction mixture was added 0.1 ml of a 30% ethanol solution of methylamine, and the mixture was further stirred for 1 hour. Then, the reaction mixture was concentrated to dryness. The residue was dissolved in chloroform, washed with water, and dried. The product was dissolved in 1 ml of dioxane, and 0.05 ml of triethylamine and 35 mg of N-hydroxysuccinimidiyl-N-benzyloxycarbonyl glycine were added, and the mixture was heated at 80° C. for 5 hours. The reaction mixture was concentrated to dryness. The residue was dissolved in chloroform, and the insoluble matter was separated by filtration. The chloroform layer was washed with water, and dried, followed by distilling off the solvent. The residue was separated and purified by silica gel preparative chromatography (chloroform/methanol in a ratio of 15:1) to afford 23 mg of 1,2',6'-tris-N-benzyloxycarbonyl-4-N-benzyloxycarbonylglycyl-de-O-methyl-KA-6606 VI as a colorless solid. The properties of the product were identical with those of the compound obtained in Example 7, (a).

EXAMPLE 10

De-O-methyl-KA-7038 III

KA-7038 III as a free base (302 mg) was reacted in the same way as in Example 6. On purification, 220 mg of de-O-methyl-KA-7038 III was obtained as a colorless powder having the following formula.

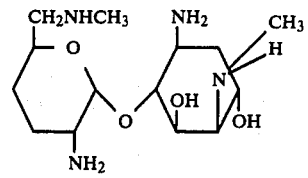

Elemental analysis: for C$_{14}$H$_{30}$N$_4$O$_4$.H$_2$O Calculated (%): C 49.98; H 9.59; N 16.65. Found (%): C 49.71 H 9.73 N 16.33.

Specific rotation: $[\alpha]_D^{25} +40°$ (c 0,5, H$_2$O).

NMR: δ D$_2$O ppm 2.80 l (3H, s, N-C$\underline{H}_3$); 2.84 (3H, s, N-C$\underline{H}_3$); 5.53 (1H, d, J=3.3 Hz, anomeric $\underline{H}$).

EXAMPLE 11

(a) Tetrakis-N-benzyloxycarbonyl-de-O-methyl-KA-7038 I

De-O-methyl-KA-7038 III (190 mg) was reacted in the same way as in Example 7, (a). On purification, 350 mg of 1,2',6'-tris-N-benzyloxycarbonyl-4-N-benzyloxycarbonylglycyl-de-O-methyl-KA-7038 III, i.e. tetrakis-N-benzyloxycarbonyl-de-O-methyl-KA-7038 I, was obtained as a colorless solid.

Elemental analysis: for C$_{48}$H$_{57}$N$_5$O$_{13}$: Calculated (%): C 63.22; H 6.30; N 7.68. Found (%): C 63.01; H 6.49; N 7.42.

Specific rotation: $[\alpha]_D^{25} +55°$ (c 1, CHCl$_3$)

NMR: δ CDCl$_3$ ppm: 2.92 (6H, s, 2xN-C$\underline{H}_3$).

(b) De-O-methyl-KA-7038 I

Tetrakis-N-benzyloxycarbonyl-de-O-methyl-KA-7038 I (320 mg) was treated in the same way as in Example 7, (b) to afford 112 mg of de-O-methyl-KA-7038 I as a colorless solid having the following formula.

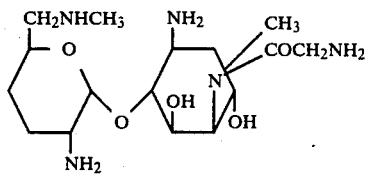

Elemental analysis: for C$_{16}$H$_{33}$N$_5$O$_5$.H$_2$O. Calculated (%): C 48.84; H 8.97; N 17.80. Found (%): C 48.54; H 8.69; N 17.98.

Specific rotation: $[\alpha]_D^{25} +126°$ (c 1, H$_2$O)

NMR: δ D$_2$O ppm: 2.83 (3H, s, 6'-N-C$\underline{H}_3$); 3.63 (3H, s, 4-N-C$\underline{H}_3$); 5.42 (1H, d, J=3 Hz, anomeric $\underline{H}$).

EXAMPLE 12

(a)

1,2′,6′-tris-N-benzyloxycarbonyl-4-N-[(S)-4-benzyloxycarbonylamino-2-hydroxybutylyl]-5-de-O-methyl-KA-6606 II 138 mg of 1,2′,6′-tris-N-benzyloxycarbonyl-5-de-methyl-KA-6606 II (1) was dissolved in 4 ml of dioxane, and 130 mg of N-hydroxysuccinimide ester of (S)-4-N-benzyloxycarbonylamine-2-hydroxybutyric acid and 0.1 ml of triethylamine were added. The mixture was heated at 55° C. for 3 hours. The reaction mixture was concentrated to dryness. The residue was dissolved in 20 ml of chloroform, washed with water, and dried, and then the solvent was distilled off. The residue was eluted with chloroform-methanol (30:1) by silica gel column chromatography, and finished in a customary manner to afford 160 mg of the desired product as a colorless solid.

NMR: δ CDCl, ppm: 3.04 (3H, s, N-C$\underline{H}_3$); 1.03 (3H, d, J=7.0 Hz, C-C$\underline{H}_3$).

IR: ν1625 cm$^{-1}$ (amide I).

Elemental analysis: for $C_{50}H_{61}N_5O_{14}$; Calculated (%): C 62.81; H 6.43; N 7.32. Found (%): C 62.55; H 6.19; N 7.48.

(b)

1,2′,6′-tris-N-benzyloxycarbonyl-4-N-[(S)-4-benzyloxycarbonylamino-2-hydroxybutyl]-5-de-O-methyl-KA-6606 II 160 mg of the product obtained in (a) above was dissolved in 3.2 ml of 1 M diborane- tetrahydrofuran solution, and reacted at room temperature for 2 hours in a stream of nitrogen. Water (0.2 ml) was added to the reaction mixture, and the mixture was concentrated to dryness. The residue was dissolved in 3 ml of 0.2 N HCl-methanol solution, and the solution was allowed to stand overnight at room temperature. The reaction mixture was concentrated to dryness. The residue was dissolved in 15 ml of chloroform, washed with a saturated aqueous solution of sodium bicarbonate and then with water, and dried. The solvent was distilled off. The residue was eluted with chloroform-methanol (20:1) by silica gel column chromatography, and finished in a customary manner to afford 85 mg of the desired product as a colorless dolid.

NMR: δ CDCl$_3$, ppm: 2.40 (3H, s, N-C$\underline{H}_3$); 1.03 (3H, d, J=7.0 Hz, C-C$\underline{H}_3$).

IR: absorption at 1625 cm$^{-1}$ disappeared

Elemental analysis: for $C_{50}H_{63}N_5O_{13}$: Calculated (%): C 63.75; H 6.74; N 7.43. Found (%): C 63.88; H 6.48; N 7.31.

(c)

4-N-[(S)-4-amino-2-hydroxybutyl]-5-de-O-methyl-KA-6606 II 80 mg of the product obtained in (b) above was dissolved in 2 ml of acetic acid, and 20 mg of 5% palladium carbon was added. It was catalytically reduced at room temperature. The reaction mixture was filtered, and the filtrate was diluted with 300 ml of water, followed by neutralization with aqueous ammonia. The mixture was then charged on a column of CM-Sephadex C-25 (NH$_4^+$ form), and developed by a gradient method with aqueous ammonia varying gradually in concentration from 0.25 N to 0.60 N. Fractions containing the desired product were collected, and lyophilized to afford 21 mg of the desired product as a colorless powder.

NMR: δ D$_2$O, ppm: 1.60 (3H, d, J=7.1 Hz, C-C$\underline{H}_3$); 3.00 (3H, s, N-C$\underline{H}_3$); 5.46 (1−H, d, J=3.5 Hz, anomeric $\underline{H}$).

Elemental analysis: for $C_{18}H_{39}N_5O_5 \cdot H_2O$: Calculated (%): C 51.04; H 9.76; N 16.54. Found (%): C 50.87; H 9.92; N 16.40.

EXAMPLE 13

(a)

1,2′,6′-tris-N-benzyloxycarbonyl-4-N-(2-benzyloxycarbonylaminoethyl)-5-de-O-methyl-KA-6606 II 500 mg of the tetrakis-N-benzyloxycarbonyl-5-de-O-methyl-KA-6606 I obtained in Example 2, (a) was treated in the same way as in Example 12, (b) to afford 220 mg of the captioned product.

NMR: δ COCl$_3$, ppm: 1.03 (3H, d, J=7.0 Hz, C-C$\underline{H}_3$); 2.43 (3H, s, N-C$\underline{H}_3$).

Elemental analysis: for $C_{48}H_{59}N_5O_{12}$: Calculated (%): C 64.20; H 6.62; N 7.80. Found (%): C 64.13; H 6.73; N 7.61.

(b) 4-N-(2-aminoethyl)-5-de-O-methyl-KA-6606 II 240 mg of the product obtained in (a) above was treated in the same way as in Example 12, (c) to afford 62 mg of the captioned product.

NMR: δ D$_2$O, ppm 1.53 (3H, d, J=7.0 Hz, C-C$\underline{H}_3$); 2.96 (3H, s, N-C$\underline{H}_3$); 5.44 (1H, d, J=3.5 Hz, anomeric H).

Elemental analysis: for $C_{16}H_{35}N_5O_4 \cdot H_2O$: Calculated (%): C 50.64; H 9.83; N 18.45. Found (%): C 50.29; H 9.71; N 18.18.

What we claim is:

1. A compound of the following formula

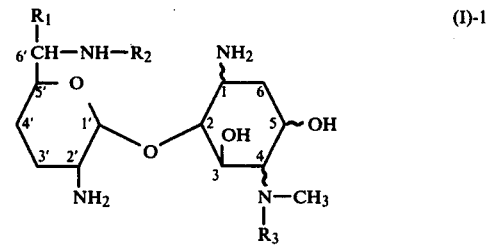

wherein R$_1$ and R$_2$ are identical or different and each represents a hydrogen atom or a methyl group, R$_3$ represents a hydrogen atom or an unsubstituted or substituted aminoacyl group having 2 to 4 carbon atoms in the acyl moiety, the substituent being selected from the group consisting of hydroxy, formyl, and carbamoyl, and when all of R$_1$, R$_2$ and R$_3$ are hydrogen atoms, the methylamino group at the 4-position is not oriented trans to the hydroxyl groups at the 3- and 5-positions; or a pharmaceutically acceptable acid addition salt thereof.

2. An antibiotic composition which comprises
 (i) an antibiotically effective amount of a compound having the following formula

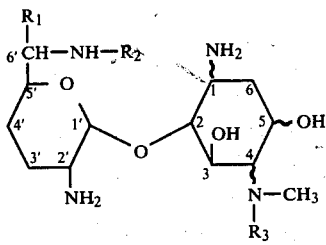

wherein $R_1$ and $R_2$ are identical or different, and each represents a hydrogen atom or a methyl group, and $R_3$ represents a hydrogen atom or an unsubstituted or substituted aminoacyl group having 2 to 4 carbon atoms in the acyl moiety, the substituent being selected from the group consisting of hydroxy, formyl, and carbamoyl, and when all of $R_1$, $R_2$ and $R_3$ are hydrogen atoms, the methylamino group at the 4-position is not oriented trans to the hydroxyl groups at the 3- and 5-positions, or a pharmaceutically acceptable acid addition salt thereof, and (ii) a pharmaceutically acceptable diluent or carrier.

3. The antibiotic composition of claim 2 wherein the amount of the compound of formula (I)-1 or its pharmaceutically acceptable acid addition salt is about 0.01 to 99.5% by weight based on the weight of the composition.

4. A process for producing a compound of the formula

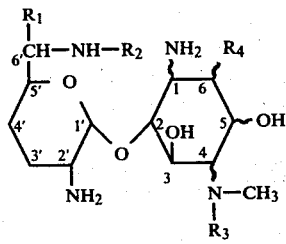

wherein $R_1$ and $R_2$ are identical or different, and each represents a hydrogen atom or a methyl group, $R_3$ represents a hydrogen atom, or an aminoacyl group having 2 to 4 carbon atoms in the acyl moiety, said aminoacyl group being unsubstituted or substituted by a member of the group consisting of hydroxy, formyl or carbamoyl, and $R_4$ represents a hydrogen atom or a hydroxyl group, or a pharmaceutically acceptable acid addition salt thereof, which comprises treating a compound of the following formula

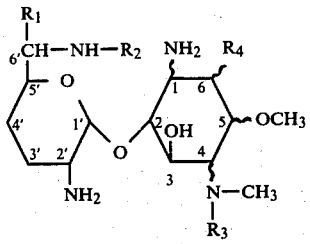

wherein $R_1$, $R_2$ and $R_4$ are as defined above, and $R_3'$ represents a moiety selected from the group consisting of a hydrogen atom, —COCH$_2$NH$_2$, —COCH$_2$NHCONH$_2$ and —COCH$_2$NHCHO, with a strong acid, and when a compound of formula (I) wherein $R_3$ is a hydrogen atom is obtained, reacting the compound with an active ester having a benzyloxycarbonyl group or a tertiary butoxy carbonyl group to protect the amino groups at the 1- and 2'-positions or the amino or methylamino group at the 6'-position of the resulting compound, then acylating it with hydroxyl, formyl- or carbamoyl-substituted or unsubstituted amino acid having 2 to 4 carbon atoms in the acyl moiety and a protected amino group or a reactive derivative thereof selected from the group consisting of a halide of the amino acid, an active ester of the amino acid, an azide of the amino acid and an anhydride of the amino acid, and then catalytically reducing the product thus obtained to split off the protective group.

5. A compound of the formula

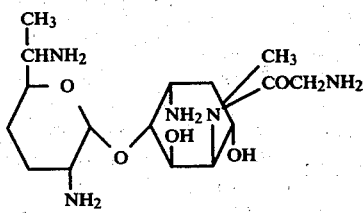

* * * * *

REEXAMINATION CERTIFICATE (287th)

United States Patent [19]
Watanabe et al.

[11] B1 4,255,421
[45] Certificate Issued Dec. 18, 1984

[54] [FORTIMICIN] AMINOGLYCOSIDES, PROCESS FOR PRODUCTION THEREOF, AND USE THEREOF

[75] Inventors: Isamu Watanabe; Akio Iwasaki; Toshihito Mori, all of Higashimurayama, Japan

[73] Assignee: Kowa Company, Ltd., Nagoya, Japan

Reexamination Request:
No. 90/000,487, Jan. 18, 1984

Reexamination Certificate for:
Patent No.: 4,255,421
Issued: Mar. 10, 1981
Appl. No.: 85,058
Filed: Oct. 12, 1979

[30] Foreign Application Priority Data
Oct. 18, 1978 [JP] Japan .................. 53-127388
Jun. 20, 1979 [JP] Japan .................. 54-76768

[51] Int. Cl.$^3$ .................. A61K 31/71; C07H 15/22
[52] U.S. Cl. .................. 424/180; 536/16.1; 536/16.8
[58] Field of Search .................. 424/180; 536/16.1, 16.8

[56] References Cited
U.S. PATENT DOCUMENTS

| | | | |
|---|---|---|---|
| 4,124,756 | 11/1978 | Martin et al. | 536/17 |
| 4,187,297 | 2/1980 | Martin et al. | 424/180 |
| 4,206,206 | 6/1980 | Mori et al. | 424/181 |
| 4,218,442 | 8/1980 | McAlpine et al. | 424/180 |
| 4,230,848 | 10/1980 | Rosenbrook | 536/17 R |
| 4,242,503 | 12/1980 | Lartey et al. | 536/17 R |
| 4,251,516 | 2/1981 | Martin et al. | 424/180 |
| 4,312,858 | 1/1982 | Deushi et al. | 424/181 |
| 4,328,307 | 5/1982 | Mori et al. | 435/80 |
| 4,329,426 | 5/1982 | Deushi et al. | 435/80 |
| 4,330,673 | 5/1982 | Rosenbrook | 536/16.1 |
| 4,389,486 | 6/1983 | Mori et al. | 435/253 |

*Primary Examiner*—Johnnie R. Brown

[57] ABSTRACT

Novel aminoglycosides of the following formula

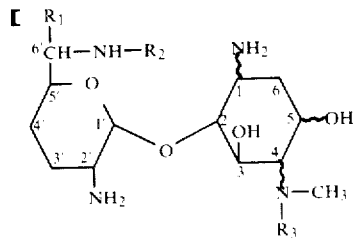

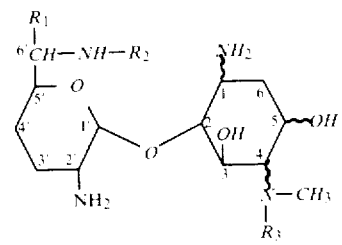

wherein $R_1$ and $R_2$ are identical or different and each represents a hydrogen atom or a methyl group, $R_3$ represents a hydrogen atom or an optionally substituted aminoacyl group having 2 to 4 carbon atoms in the acyl moiety, and when all of $R_1$, $R_2$ and $R_3$ are hydrogen atoms, the methylamino group at the 4-position is not oriented trans to the hydroxyl groups at the 3- and 5-positions; and acid addition salts thereof, which are useful as antibiotics; and process for producing compounds containing the same.

REEXAMINATION CERTIFICATE ISSUED UNDER 35 U.S.C. 307.

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 1 to 4 as follows:

[FORTIMICIN] *AMINOGLYCOSIDES, PROCESS FOR PRODUCTION THEREOF, AND USE THEREOF*

Column 3, lines 63-68 and Column 4, lines 1-12:
The specification of the German OLS 2813021 discloses in detail the separation of KA-6606 I [and] *to* IV corresponding to formula (A), KA-6606 V and VI can be separated similarly during the separation of KA-6606 I to IV from crude KA-6606 obtained in the manner disclosed in the above German specification. For example, the crude KA-6606 is caused to be adsorbed to an adsorbent such as a weak acid-type cation exchange resin, CM-Sephadex or CM-cellulose, and eluted by a gradient method or a stepwise method using aqueous ammonia, an aqueous solution of ammonium carbonate, an aqueous solution of ammonium formate, etc. First, several trace components are eluted, and KA-6606 IV and then KA-6606 III are eluted as free bases. On further elution, KA-6606 I, VI and II substances are sequentially separated, and finally KA-6606 V is separated.

Column 6, lines 41-51:
Since the substance KA-7038 is a water-soluble basic substance but difficultly soluble in common organic solvents, it can be separated from the culture broth by utilizing the procedures which are customarily used in isolating and purifying water-soluble basic antibiotics. For example, there can be used an adsorption desorption method using [and] *an* ion exchange resin, active carbon etc.; column chromatographic method using cellulose, silica gel, alumina, etc.; and a method for extracting with butanol, amyl alcohol, etc. using a higher fatty acid as an adjuvant.

Column 8, lines 54-65:
However, this method is commercially disadvantageous because the yield in the first step of cleaving the methyl ether is only about 1.3%. According to this invention, de-O-methyl products can be obtained in commercially feasible yields from fortimicins and KA-6606 and KA-7038 substances having a structure similar thereto. Specifically, the compounds of formula [(II)-2] *(I)* can be obtained in a yield as high as or more than 10 times that obtained in the aforesaid known method by treating the compound of formula (II) with strong acids.

Column 21, lines 1-6:

EXAMPLE 12

(a)

1,2',6'-tris-N-benzyloxycarbonyl-4-N-[(S)-4-benzylox-[ycarbonylamino-2-hydroxybutyryl]-5-de-O-methyl-] *ycarbonylamino-2-hydroxybutyryl]-5-de-O-methyl* KA-6066 II

AS A RESULT OF REEXAMINATION, IT HAS BEEN DETERMINED THAT:

The patentability of claim 5 is confirmed.

Claims 1-4 are cancelled.

New claims 6-13 are added and determined to be patentable.

6. A compound of the formula

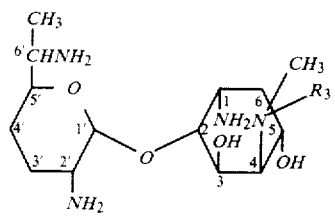

wherein $R_3$ represents hydrogen, glycyl, carbamoylglycyl or formylglycyl or a pharmaceutically acceptable acid addition salt thereof.

7. A compound of the formula

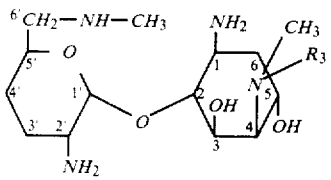

wherein $R_3$ represents hydrogen, glycyl, carbamoylglycyl or formylglycyl or a pharmaceutically acceptable salt thereof.

8. An antibiotic composition which comprises
(i) an antibiotically effective amount of a compound having the following formula

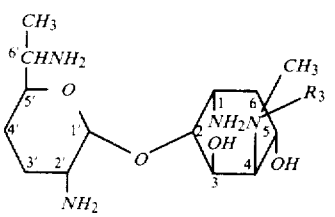

wherein $R_3$ represents hydrogen, glycyl, carbamoylglycyl or formylglycyl or a pharmaceutically acceptable acid addition salt thereof, and
(ii) a pharmaceutically acceptable diluent or carrier.

9. An antibiotic composition of claim 8 wherein the amount of the compound of the formula set forth or its pharmaceutically acceptable acid addition salt is about 0.01 to 99.5% by weight based on the weight of the composition.

10. An antibiotic composition which comprises
(i) an antibiotically effective amount of a compound having the following formula

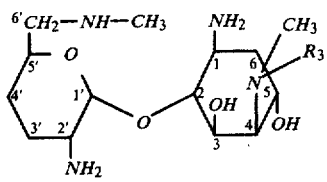

wherein $R_3$ represents hydrogen, glycyl, carbamoylglycyl or formylglycyl or a pharmaceutically acceptable acid addition salt thereof, and
(ii) a pharmaceutically acceptable diluent or carrier.

11. An antibiotic composition of claim 10 wherein the amount of the compound of the formula set forth or its pharmaceutically acceptable acid addition salt is about 0.01 to 99.5% by weight based on the weight of the composition.

12. A process for producing a compound of the formula

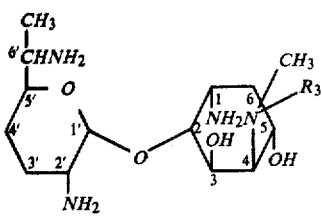

wherein $R_3$ represents hydrogen, glycyl, carbamoylglycyl or formylglycyl or a pharmaceutically acceptable acid addition salt thereof, which comprises treating a compound of the formula

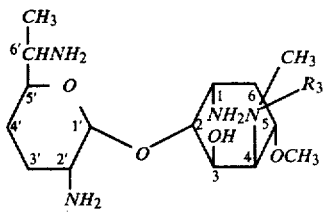

wherein $R_3'$ represents hydrogen, glycyl, carbamoylglycyl or formylglycyl with a Lewis acid or a mineral acid, and when a compound of the formula wherein $R_3$ is a hydrogen atom is obtained, reacting the compound with an active ester having a benzyloxycarbonyl group to protect the amino groups at the 1,2'- and 6'-positions of the resulting compound, then acylating it with glycine, protected glycine, carbamoylglycine, formylglycine or a reactive derivative thereof selected from the group consisting of a halide of the amino acid, an active ester of the amino acid, an azide of the amino acid and an anhydride of the amino acid, and then catalytically reducing the product thus obtained to split off the protective group.

13. A process for producing a compound of the formula

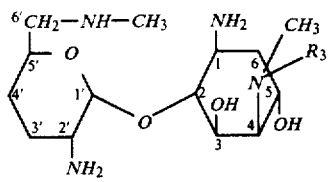

wherein $R_3$ represents hydrogen, glycyl, carbamoylglycyl or formylglycyl or a pharmaceutically acceptable acid addition salt thereof, which comprises treating a compound of the formula

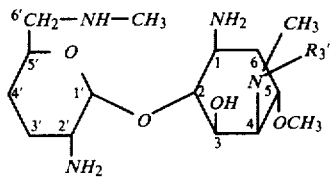

wherein $R_3'$ represents hydrogen, glycyl, carbamoylglycyl or formylglycyl with a Lewis acid or a mineral acid, and when a compound of the formula wherein $R_3$ is a hydrogen atom is obtained, reacting the compound with an active ester having a benzyloxycarbonyl group to protect the amino groups at the 1,2'- and 6'-positions of the resulting compound, then acylating it with glycine, protected glycine, carbamoylglycine, formylglycine or a reactive derivative thereof, selected from the group consisting of a halide of the amino acid, an active ester of the amino acid, an azide of the amino acid and an anhydride of the amino acid, and then catalytically reducing the product thus obtained to split off the protective group.

* * * * *